(12) United States Patent
Brasey et al.

(10) Patent No.: US 11,681,398 B2
(45) Date of Patent: Jun. 20, 2023

(54) CONTROL SYSTEM WITH REMOVABLE STERILIZABLE BUTTON

(71) Applicant: Bien-Air Holding SA, Bienne (CH)

(72) Inventors: Yvan Brasey, Gletterens (CH); Corentin Zill, Courtelary (CH); Davide Sarchi, Zurich (CH)

(73) Assignee: BIEN-AIR HOLDING SA, Bienne (CH)

( * ) Notice: Subject to any disclaimer, the term of this patent is extended or adjusted under 35 U.S.C. 154(b) by 915 days.

(21) Appl. No.: 16/532,832

(22) Filed: Aug. 6, 2019

(65) Prior Publication Data
US 2020/0046330 A1 Feb. 13, 2020

(30) Foreign Application Priority Data
Aug. 13, 2018 (EP) .................................... 18188657

(51) Int. Cl.
| | |
|---|---|
| *E05B 1/00* | (2006.01) |
| *A61L 2/26* | (2006.01) |
| *G05G 1/04* | (2006.01) |
| *A61B 17/00* | (2006.01) |
| *A61B 90/00* | (2016.01) |
| *G06F 3/044* | (2006.01) |
| *G06F 3/033* | (2013.01) |

(52) U.S. Cl.
CPC .............. *G06F 3/044* (2013.01); *A61L 2/26* (2013.01); *E05B 1/0069* (2013.01); *G05G 1/04* (2013.01); *G06F 3/033* (2013.01); *A61B 2017/00017* (2013.01); *A61B 2017/00477* (2013.01); *A61B 2017/00876* (2013.01); *A61B 2090/0813* (2016.02)

(58) Field of Classification Search
None
See application file for complete search history.

(56) References Cited

U.S. PATENT DOCUMENTS

| | | | |
|---|---|---|---|
| 2004/0125437 A1 | 7/2004 | Schmidt et al. | |
| 2010/0286791 A1* | 11/2010 | Goldsmith | ....... A61B 17/12022 604/524 |
| 2014/0035834 A1* | 2/2014 | Sharma | ................. G06F 1/1669 345/173 |
| 2015/0150646 A1* | 6/2015 | Pryor | .................... G06F 3/0354 345/184 |

FOREIGN PATENT DOCUMENTS

| | | |
|---|---|---|
| CN | 101444631 A | 6/2009 |
| WO | 2014060676 A1 | 4/2014 |

OTHER PUBLICATIONS

Search Report issued in European Patent Application No. 18188657.3 dated Dec. 20, 2018, 8 pages.

* cited by examiner

*Primary Examiner* — Stephen T. Reed
(74) *Attorney, Agent, or Firm* — Pearne & Gordon LLP

(57) ABSTRACT

The present invention concerns a control system (1) for a micro-motor for dental or surgical use comprising a control box (10) provided with an adjustment knob (2), mounted in a way rotatable about a rotational axis (A-A). The adjustment knob (2) is made up of a control support (20) integral with an encoder (3) integrated in the said box (10), and a sterilizable button (21) coupled in a removable way to the said control support (20).

13 Claims, 5 Drawing Sheets

CONTROL SYSTEM WITH REMOVABLE STERILIZABLE BUTTON

TECHNICAL FIELD OF THE INVENTION

The present invention relates to the field of instruments and apparatus for practitioners in the medical field, such as dentists and dental surgeons. More specifically, it concerns a control device for the motor of such apparatuses.

STATE OF THE ART

Dentists, hygienists and dental surgeons, as well as other practitioners of the field in particular of endodontics, periodontology and oral surgery or of implantology often have available various instruments and devices equipped with a rotary tool actuated by an electric motor (micro-motor). These motors have a predetermined power output, which is adapted to the operations to be carried out. Thus, for example, depending on the applications involved (cleaning, polishing, root treatment, etc.), the milling or grinding operations require the use of different speeds or different couplings adapted to the contact force exerted on the tool making it possible to generate efficiently the level of abrasion or drilling without the tool overheating excessively, which could damage the surrounding tissue.

Various control units are available on the market to control the micro-motors of such tools. The control station Optima of the patent applicant makes it possible, for example, to carry out prophylactic or restorative procedures by providing an alternative to the turbines, usually used for this type of operations, but which have the drawback of a much higher noise level owing to the very high rotational speed (greater than 100000 revolutions per minute) of such pneumatically driven tools. In this case the speed is controlled by a central wheel or roller located on the front face of the console, designed specifically and exclusively for this purpose.

In the field of implantology and maxillo-facial surgery, other types of control units are known, such as the Chiropro of the patent applicant, which is equipped with a control screen and several control keys arranged on a substantially flat keyboard. The different modes of operations are selected notably with the aid of arrows and are actuated with the aid of a central confirmation key. A first drawback of this type of console lies in the relatively poor ergonomic nature of the control interface, often requiring numerous successive key strokes on the different buttons to change the program. A second disadvantage of this type of control unit has to do with the disinfection and decontamination process of the console's keyboard, which with each procedure risks being completely contaminated as a result of the surgeon's various manipulations. Such a process proves to be relatively tedious because it is impossible to sterilize the entire console by heating it to 135° C., according to recommended procedures, without damaging it seriously. It is therefore necessary to carry out only a manual disinfection with chemical substances, which can often act aggressively on the materials of the console, thus leading to a deterioration of the aesthetic appearance in the medium or long term.

There thus exists a need for control interface solutions not having the above-mentioned drawbacks.

SUMMARY OF INVENTION

The invention has as object to provide a control system equipped with a simple interface, practical to use, and easy to sterilize if need be.

This object is achieved according to the invention by means of a control system for a micro-motor for dental or surgical use comprising a control box provided with an adjustment knob as herein described, wherein the adjustment knob is made up of a control support integral with an encoder integrated in the box, and a sterilizable button coupled in removable fashion to the control support. By means of this arrangement of the adjustment knob, it is possible to easily assemble and disassemble the part handled by the surgeon and to sterilize the latter independently from the rest of the control box. Moreover, the sterilizable part can from now on be considered a wearing part able to be replaced in a modular way, independently from the rest of the control system, and this piece can therefore be sterilized and cleaned with more aggressive and more effective chemical substances.

Preferably, the coupling is achieved through friction, through snap-on connection, or magnetically, which makes possible a manual assembly or disassembly of the removable sterilizable button, i.e. without the aid of any auxiliary tool. The convenience of use is thus greatly enhanced for this type of operation of assembling and replacing of the removable sterilizable part.

According to one preferred embodiment, the adjustment knob is provided both for the selection in rotation and for the activation by pressing of functions which are displayable on a control screen of the box, which makes it possible to enhance the level of ergonomics with respect to existing products in which these two functionalities were until now achievable with the aid of separate activating elements.

According to a preferred embodiment, the removable sterilizable button is terminated, at its lower end, by a collar extending radially towards the exterior, which has the advantage, on the one hand, of preventing any inadvertent contamination of the box during the manipulation of the adjustment knob, and, on the other hand, of facilitating the disassembly of the removable sterilizable button by increasing the diameter of the object in the grasping zone and thus facilitating manual gripping. Moreover, in the case where pressing is necessary on the knob, this can likewise be carried out more easily by pressing the fingers on the outer surface of the collar.

According to a preferred embodiment, the removable sterilizable button is preferably coupled to the control support in such a way that, in assembled position, an operational play of at least 0.2 mm exists axially between the lower end of the sterilizable button and the outer surface of the box when it is at rest, that is to say in non-pressed position. Thus, the fingers can pass slightly behind the button to grasp it and easily extract it from the box during an operation of disassembly.

According to a preferred embodiment, the removable sterilizable button has a central cavity provided with at least one first inner contact surface for coupling to a bearing surface, and means of axial retention and of driving in rotation arranged on either side of the removable sterilizable button and of the control support. Such an arrangement makes it possible to easily bring the removable sterilizable button to abut against the control support during assembly, all the while ensuring good functioning quality of the knob which can thus easily transmit in an efficient way the actuating torque and prevent at the same time any risk of involuntary pulling out of the removable sterilizable button. Moreover, the coupling mechanism is hidden under the cover of the button, which makes it possible to better preserve the aesthetics of the control device, despite the operational improvements provided.

Preferably, the central cavity of the said removable sterilizable button comes out into an inner peripheral shoulder. Such an arrangement aims to ensure the consistency of the quality of the coupling between the removable sterilizable button and the control support independently of manufacturing dimensions, which can fluctuate slightly for each of these pieces depending on assembly tolerances. The quality of this coupling makes it possible in particular to ensure a good systematic transmission of the torque to the encoder.

According to an especially preferred embodiment, the removable sterilizable button is coupled magnetically to the control support, one active magnetic piece being integrated in the support and one passive magnetic piece being integrated in the removable sterilizable button, the intensity of the exerted magnetic force being in the range between 5 and 15 Newton. Such an arrangement makes it possible to provide an excellent compromise between the quality of the hold of the button on its support and the ease of assembly/disassembly operations.

According to a preferred variant connected with such a magnetic coupling mode, the removable sterilizable button comprises a central cavity, as according to a preferred embodiment previously described, but which contains moreover a second conical inner contact surface, brought to rest, in assembled position of the adjustment knob, against a lateral coupling surface of the control support, and these surfaces have an inclination of 15 degrees with respect to the axis of rotation (A-A) of the adjustment knob. Such an arrangement for the coupling makes possible a very simple construction for machining not requiring any surface or element for hooking nor elements for driving in rotation because the orientation of the magnetic field lines permits an optimal transmission of the torque.

According to another preferred variant, still connected with the magnetic mode of coupling, the active magnetic piece integrated in the control support is a first permanent magnet arranged in such a way as to have a magnetization oriented perpendicularly with respect to the axis of rotation of the adjustment knob, and a second permanent magnet is integrated in the removable sterilizable button in such a way as to have a magnetization oriented parallel to the first permanent magnet. In such a configuration, not just a force of attraction establishes itself between the button and the support, but a magnetic torque between the button and the support exerted via the two permanent magnets will naturally align the button on the support when it is put in position, which will position the latter in a predefined indexed angular position, on the one hand, and, on the other hand, will make it possible to drive in rotation even more efficiently the support at the time of manual rotation of the button owing to the natural tendency to preserve the alignment of the poles of the two magnets.

According to still another preferred variant connected with the magnetic mode of coupling, the active magnetic piece integrated in the control support is a first permanent magnet arranged in such a way as to have a magnetization oriented this time directly along the axis of rotation (A-A) of the adjustment knob, and a second permanent magnet is integrated in the removable sterilizable button in such a way as to have a magnetization likewise oriented along the axis of rotation (A-A) of the adjustment knob, but in the opposite direction with respect to that of this first permanent magnet. Such a configuration of magnets in polarity opposition facing each other makes it possible to establish a force of repulsion between the button and the support when they are distant from one another, and to ensure simultaneously a great force of magnetic attraction when the button is brought into proximity to the support, and this owing to the deviation of the magnetic field lines caused by the ferromagnetic component (i.e. the passive magnetic piece) integrated in the cover of the button. Thus during the phase of positioning of the button, the user will feel initially a resistance and then an effect of automatic snap-on connection of the button on the support, simulating the feel of a mechanical snap-on connection. During the phase of disassembly of the button, it will suffice, on the other hand, for the user to move the button slightly away or to incline it with respect to the axis of the support to take advantage of a force of magnetic repulsion favoring its extraction, which will make it possible to avoid even more efficiently any involuntary contact between the contaminated button and the screen or any other part of the control box.

According to an alternative embodiment, the removable sterilizable button can be is coupled by friction to the control support by means of O-ring type seals inserted in lateral coupling recesses made either on the removable sterilizable button or the control support of the adjustment knob. One advantage of the given solution is to be able to use the same elements at the same time for the axial retention and the driving in rotation, i.e. the transmission of the torque. However, compared with the magnetic coupling mode, the service life is substantially reduced and the O-rings must be changed regularly to ensure the quality of the coupling.

According to another embodiment, the removable sterilizable button can be coupled to the control support with the aid of elastically deformable snap-on fasteners provided with lugs intended to be inserted in hooking grooves. Such an arrangement also makes it possible to use the same elements at the same time for the axial retention and for the driving in rotation; such a solution however is subject to creep which does not make it possible to ensure the quality of the coupling in a sustainable way.

The present invention relates furthermore to a control box as well as a sterilizable button, taken independently from one another, because these two products can be sold separately, even if they concern the same proposed control system.

BRIEF DESCRIPTION OF THE DRAWINGS

Other advantages and features will follow more clearly from the description which follows of embodiments for implementation of the invention, given by way of non-limiting example and illustrated by the annexed drawings, which include.

DESCRIPTION OF PREFERRED EMBODIMENTS OF THE INVENTION

Figure 1A:
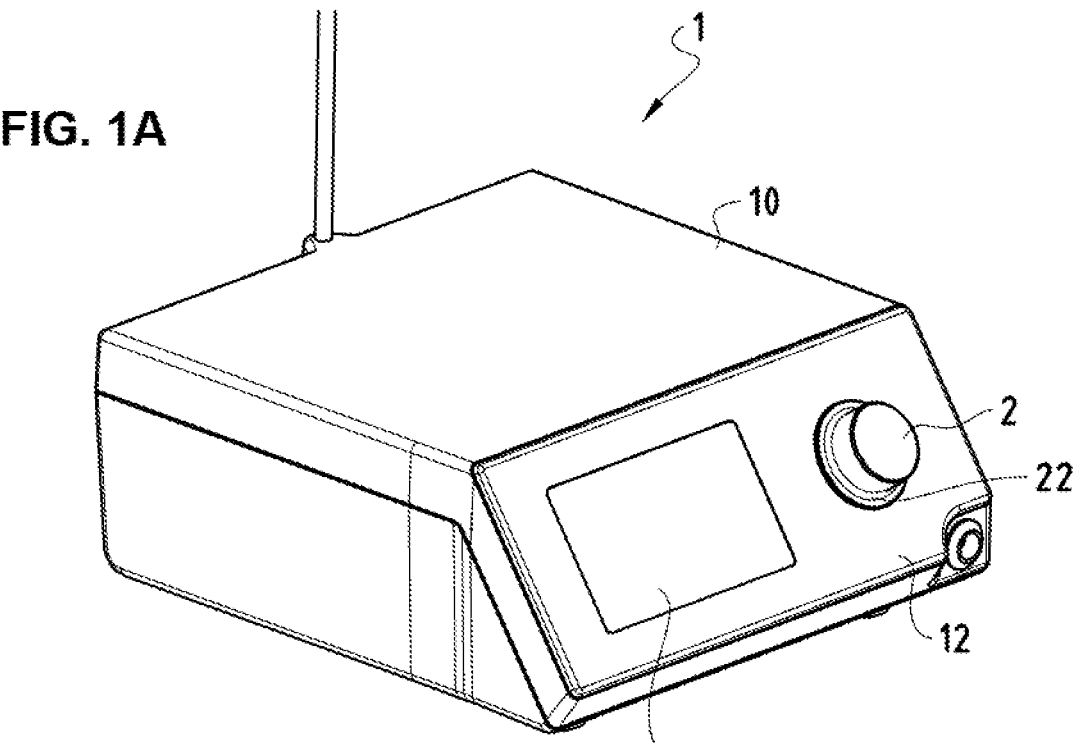
FIG. 1A is a schematic view in perspective of a control system according to a preferred embodiment of the invention, in a configuration where the adjustment knob is able to be actuated.
Figure 1B:
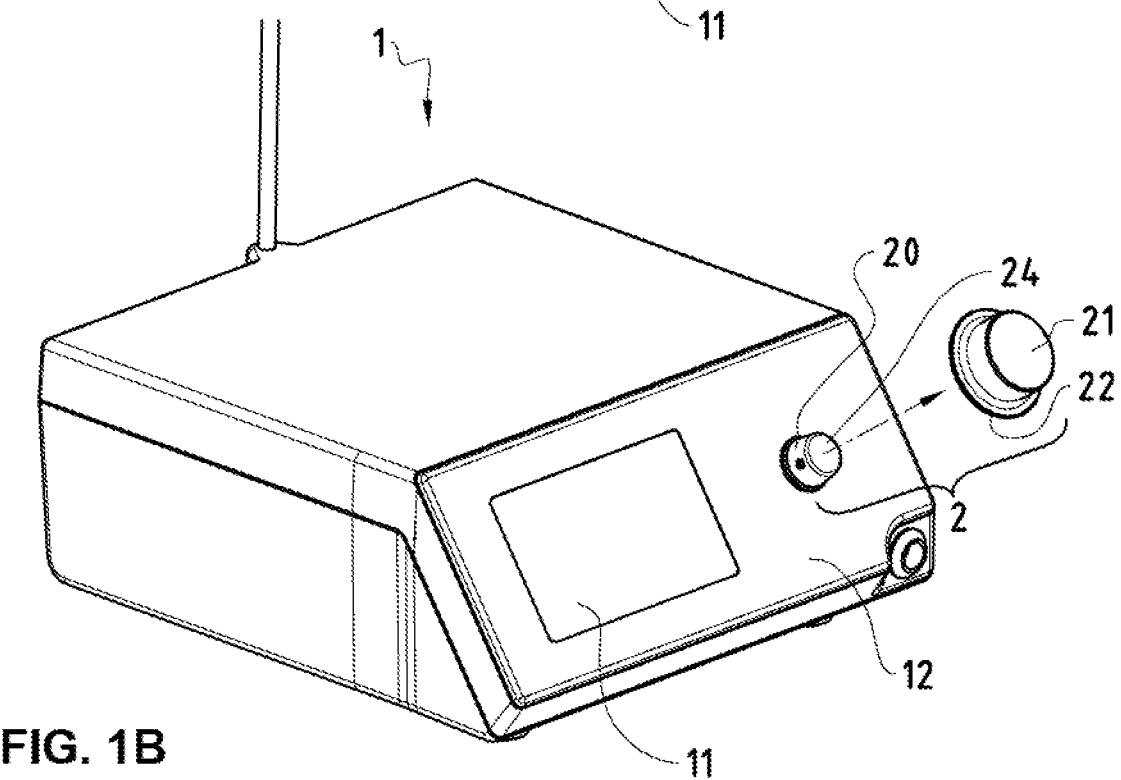
FIG. 1B is a schematic view in perspective of a control system according to a preferred embodiment of the invention, representing the removable sterilizable button of the knob in disassembled position with respect to the control box.

FIGS. 1A and 1B represent views in perspective of a control system 1 provided with a removable sterilizable button 21 according to a preferred embodiment of the present invention, using a magnetic mode of coupling. The control system 1 uses a control box 10 which comprises conventionally a control screen 11 provided on the outer surface 12 of the control box 10, as well as an adjustment knob 2, provided with an encoder—not visible in these figures but which is represented further on in particular in FIG. 3—and with which it is possible to select predefined modes or functions by making it turn in one direction or the other. Then, to validate or respectively activate the modes or functions, a slight pressing can be exerted on the knob 2. Thus, the level of ergonomics is significantly improved with respect to control systems using dedicated keys or any other dissociated elements for the selection and activation of modes or of functions.

In FIG. 1A illustrating the control system in assembled position, the adjustment knob 2 does not seem to differ from a common knob integral with the control box 10 and fixed permanently thereon; one can likewise distinguish a collar 22 terminating the knob 2, or more precisely the removable sterilizable button 21 thereof, on the side of the box. This collar 22 extends radially outwardly, which makes it possible to facilitate its being grasped during selection and activation operations all the while protecting the outer surface 12 of the control box 10 against undesired contact with the fingers. Moreover, the operation of disassembly of the removable part of the adjustment knob 2 is likewise facilitated owing to the slight increase in diameter which makes it possible to put the fingers more easily right on the removable sterilizable button 21 to grasp it with a view to detaching it from the control box 10.

In contrast, FIG. 1B illustrates the removable nature of the coupling between the sterilizable button 21 and a control support 20 integral with the box 10. The control support 20 is mounted in a rotatable way vis-à-vis the control box of the control system 1, and constitutes a first part of the adjustment knob 2, the other part being formed by a sterilizable button 21 on which a collar 22 is formed extending radially outward at its base. This arrangement thus makes it possible to sterilize more effectively and in a modular way the part which is a priori the only part which must be manipulated and thus the only part likely to require such a treatment after each use.

Figure 2:
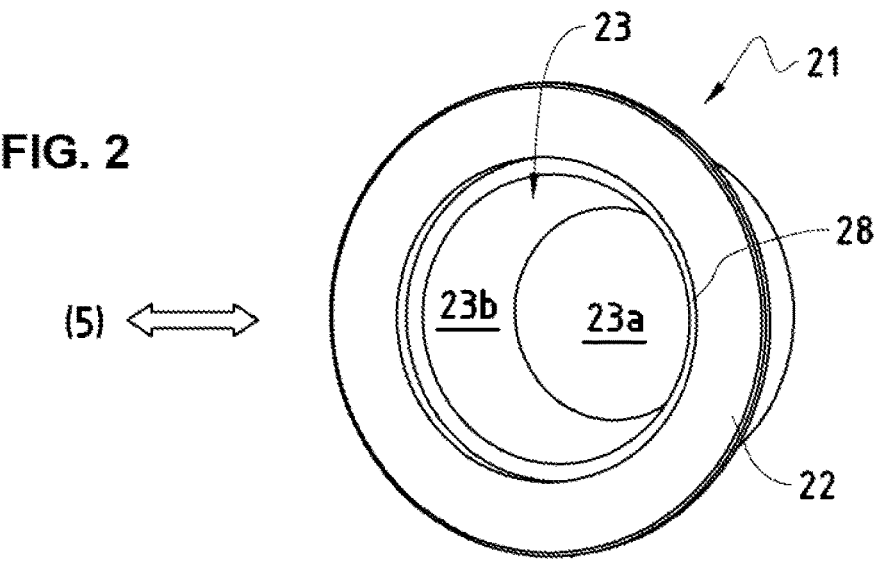
FIG. 2 is a view in perspective from below of a removable sterilizable button according to a preferred embodiment using a magnetic mode of coupling with respect to a control support.

FIG. 2 shows the removable sterilizable button 21 taken in an isolated way from the rest of the control system 1, and which can thus be sold also separately. This sterilizable button 21 is preferably made up at least partially of a ferromagnetic material such as magnetizable steel in order to constitute a passive magnetic piece 5 intended to co-operate with an active magnetic piece 4, such as a magnet disposed in the control support 20 of the adjustment knob 2. The shape of the removable sterilizable button 21 corresponds substantially to a cap, with a collar 22 extending radially at its base and allowing a central cavity 23 to appear permitting the insertion of the control support 20. The central cavity 23 is closed off by a bottom comprising a first inner contact surface 23a, preferably flat, and intended to be coupled to a bearing surface 24 of the control support 20, and having a second inner contact surface 23b, preferably conical, on which a lateral coupling surface 25 of the control support 20 comes to abut. An inner peripheral shoulder 28 is however provided to make a supplementary space at the entrance of the central cavity 23.

Figure 3:
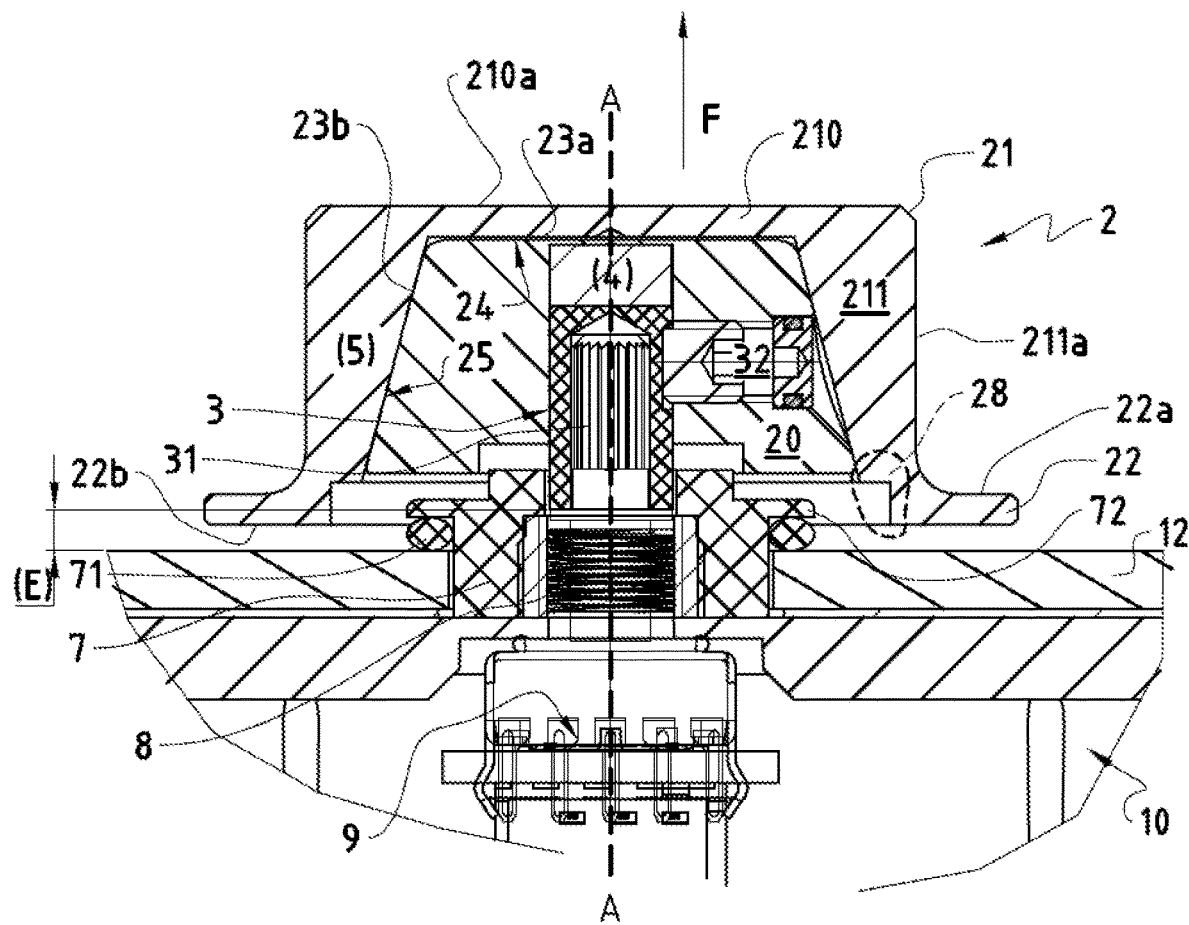
FIG. 3 is a sectional view of an adjustment knob according to a preferred embodiment using a magnetic mode of coupling, representing the removable sterilizable button in assembled position on the control support of the box.

FIG. 3 explains the mode of coupling between the control support 20 and the removable sterilizable button 21 according to a preferred embodiment of the invention, in which the coupling is magnetic and the lateral surfaces at the same time of the control support 20 and of the removable sterilizable button are conical with an inclination ranging between 10 and 20 degrees, and preferably being 15 degrees, in such a way as to have an optimal orientation with respect to the field lines generated by the magnet integrated in the control support 20 of the adjustment knob 2 and the direction of magnetization of which is oriented here perpendicularly to the axis of rotation A-A of the adjustment knob 2. According to this preferred embodiment, one thus finds an active magnetic piece 4, i.e. the permanent magnet integrated in the control support 20, while all of the removable sterilizable button 21 constitutes a passive magnetic piece 5. The cross section of the control support 20 here is trapezoidal, embodying a volume of truncated conical shape at its top. The upper part of the trapezoid thus corresponds to the bearing surface 24 of the flat support, which is brought into abutment against the first inner contact surface 23a of the removable sterilizable button 21, constituting the inner face of the cover 210. The force of magnetic attraction therefore constitutes by itself alone axial means of retention to maintain these two surfaces in abutment one against the other. Moreover, the inclination of the second inner contact surface 23b and of the lateral coupling surface 25 makes it possible, when the button is actuated in rotation by the user, to drive more efficiently in rotation the encoder 3 integrated in the control support 20, than with a co-operation of cylindrical surfaces, for which the transmission of the torque is not optimal. The encoder 3 is formed here by a threaded rod 31 mounted in a rotatable way along the axis of rotation A-A of the adjustment knob 2 with respect to the control box 10, and a screw 32 mounted perpendicularly to this axis of rotation A-A.

In FIG. 3, the cover 210 forming the upper part of the removable sterilizable button 21 can be distinguished, and the axial skirt 211 whose lateral thickness thins as one descends downward until reaching the collar 22 oriented radially outward. The external lateral surface 211a of the removable sterilizable button 21 is substantially cylindrical, in order to allow an easy gripping of the latter for a rotational actuation for a selection, typically by means of a drop-down menu. When the user must exert a pressing to validate a function or change of mode, he can press either on the upper surface of the cover 210a or on the upper surface of the collar 22a; the control support 20 will then be driven downward by going against the return force F of the spring 8 oriented upward to achieve an electrical contact of the resistive type with the electronic control circuit 9. Immediately after such an actuation, the control support 20 will be brought back into its resting position under the action of the return force F exerted by the return spring 8.

The adjustment knob 2 is mounted on an insertion tube 7 in the box, which has an upper shoulder 72 partially covering the outer surface 12 of the control box 10, and which is affixed on a tightness seal 71. However, while such an arrangement ensures excellent tightness properties with respect to the interior of the control box 10, an additional volume is nevertheless generated above the latter, and which should not impede the action of a pressing on the button—transmitted directly to the control support 20—until an electrical contact with the control circuit 9 is achieved. This is one of the reasons why the inner peripheral shoulder 28 (shown by the hatched part inside the circle of broken lines) is provided at the mouth of the central cavity 23 to provide an additional recess avoiding any possible interference with the upper shoulder 72 of the insertion tube of the knob.

Still in FIG. 3, it can be noted that the adjustment knob 2 is in pushed-in position, while the arrow indicated by the reference E defines an operational play at rest, i.e. the space between the outer surface of the box 12 and the lower surface of the collar 22b. This operational play is defined as being preferably equal to at least 0.2 millimeters, and can preferably go to 1 millimeter to allow easy gripping of the removable sterilizable button 21 and its withdrawal after use.

According to the preferred embodiment illustrated in the preceding figures where the removable sterilizable button 21 is magnetically coupling to the control support 20, only an active magnetic piece 4 is integrated in the control support 20, while removable sterilizable button 21 constitutes an entire passive magnetic piece 5, in such a way that the intensity of the magnetic force exerted preferably ranges between 5 and 15 Newton. This range of values relating to the intensity of the magnetic force allows the operations of disassembly to remain easy without necessitating abrupt or forceful movements to remove the removable sterilizable button 21. However, other variants are possible while still remaining within the scope of a magnetic mode of coupling, using, for example, a removable sterilizable button 21 only composed partially of magnetic material, or moreover by arranging permanent magnets on either side of the control support 20 and of the removable sterilizable button 21, as explained with the aid of the diagrams of FIGS. 4 and 5 which follow.

Figure 4:
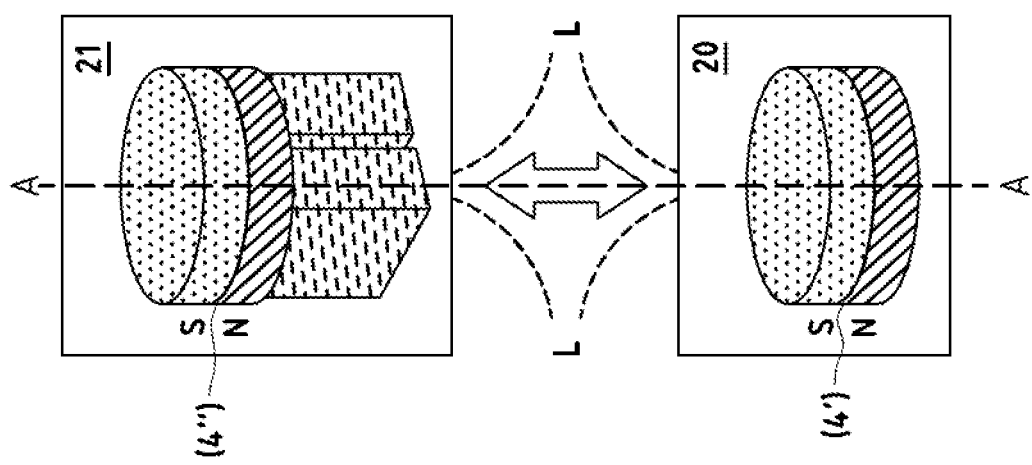
FIG. 4 illustrates schematically an alternative embodiment for a magnetic coupling using two permanent magnets arranged on either side of the control support of the box and of the removable sterilizable button, according to a magnetization direction orthogonal to the axis of rotation of the adjustment knob.
Figure 4:
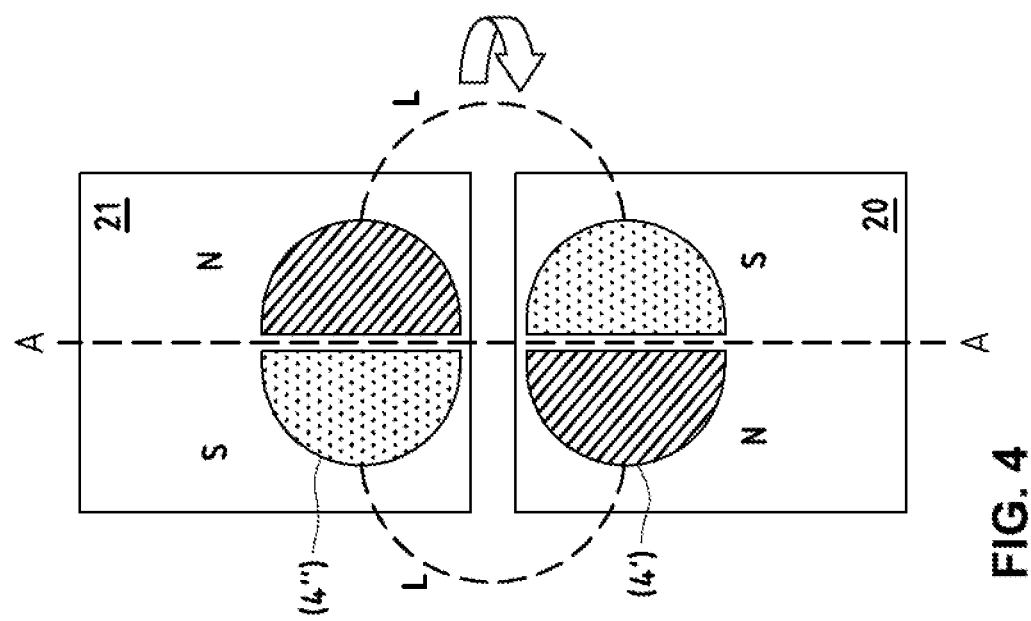

FIG. 4 illustrates schematically a preferred variant for a magnetic type of coupling between the control support 20 and the removable sterilizable button 21, according to which, in addition to a first permanent magnet 4' constituting an active magnetic piece 4 arranged in a way similar to that of FIG. 3, i.e. with a direction of magnetization orthogonal to the axis of rotation A-A of the adjustment knob 2, a second permanent magnet 4" is arranged in the removable sterilizable button 21 according to a direction of magnetization encompassed in a parallel plane, overlying that of the first permanent magnet 4'. Thus, in mounted position of the removable sterilizable button 21 on the control support 20, the two permanent magnets 4' and 4" will have a tendency to align themselves naturally along a direction of magnetization parallel with respect to one another owing to the preservation of alignment of poles following the laws of physics. In this way, two advantageous technical effects are achieved, the first being to obtain an identical angular indexing position of the removable sterilizable button 21 after each mounting on its control support 20, and the second being to ensure a still better transmission of the torque exerted on the removable sterilizable button 21 to the control support 20 at the time of actuation in rotation of the knob 2 (indicated by the arrow in clockwise direction in FIG. 4, likewise indicating the direction of the field lines L and the poles north «N» and south «S» of each magnet). This coupling variant has the advantage of dispensing, at least partially, but virtually completely, with any ferromagnetic material for the removable sterilizable button 21 to obtain the effects sought in terms of quality of transmission of torque and hold on the control support 20; however, preferred here yet again, with or without the presence of passive ferromagnetic material, will be an arrangement of permanent magnets making it possible to obtain a force of attraction included within the same range of values as those mentioned previously, i.e. between 5 and 15 Newton.

Figure 5:
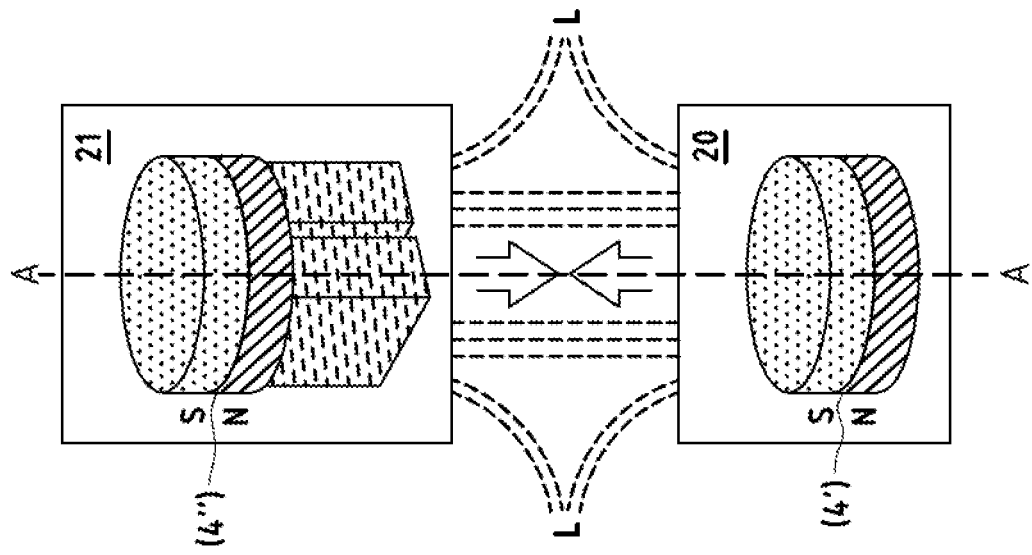
FIG. 5 illustrates schematically another alternative embodiment for a magnetic coupling using two permanent magnets arranged on either side of the control support of the box and of the removable sterilizable button, this time with a magnetization direction oriented along the axis of rotation of the adjustment knob and in polarity opposition.

FIG. 5 illustrates still another preferred variant using a magnetic coupling mode using two permanent magnets respectively arranged on either side of the control support 20 and of the removable sterilizable button 21. However, contrary to the arrangement of the preceding FIG. 4, the first permanent magnet 4' of the control support 20 and the second permanent magnet 4" of the removable sterilizable button are henceforth arranged directly along the axis of rotation A-A of the adjustment knob, and in polarity opposition (the poles north «N» of each of the magnets facing one another). Thus, as represented on the left in FIG. 5, when the removable sterilizable button 21 is substantially at a distance away from the control support 20, the field lines L of each of the magnets are directed with respect to one another in such a way that a repulsive effect, indicated by the arrow, is generated between these two pieces. However, when the removable sterilizable button 21 is sufficiently brought closer to the control support 20, as illustrated in the right-hand part of FIG. 5, the force of magnetic repulsion transforms into a force of magnetic attraction, in view of the spatial reorganization of the field lines L which tend to maximize the magnetic flow through the different components. According to this variant, the operation of mounting or assembly produces a sort of «click effect» as soon as one crosses the threshold of mutual proximity between removable sterilizable button 21 and the control support 20 transforming the force of magnetic repulsion into a force of magnetic attraction. In terms of transmission of torque and preferred orientation (angular indexation of the removable sterilizable button 21 with respect to the control support 20), the same advantages can be obtained as those provided by the preceding variant illustrated in FIG. 4; the variant of FIG. 5 has however the additional advantage of facilitating the operation of disassembly owing to the force of magnetic repulsion resulting from remoteness and/or the inclination of the removable sterilizable button 21, which favors the extraction of the latter.

The advantage common to all the preferred variants using a magnetic coupling mode between the removable sterilizable button 21 and the control support 20 is that the operations of assembly and disassembly are particularly simple, not requiring any tool, and that these operations can be repeated a very great number of times without jeopardizing the hold of the removable sterilizable button 21 on the control support 20 nor the transmission of torque exerted by the user to the encoder 3 of the adjustment knob 2. Even in the case where the magnets are inserted in the removable sterilizable button 21, it is possible, using for instance magnets made of samarium cobalt, to subject the latter to several hundred cycles of sterilization at 135° C. or more without altering their magnetic properties because their Curie temperature exceeds 300° C.

Figure 6:
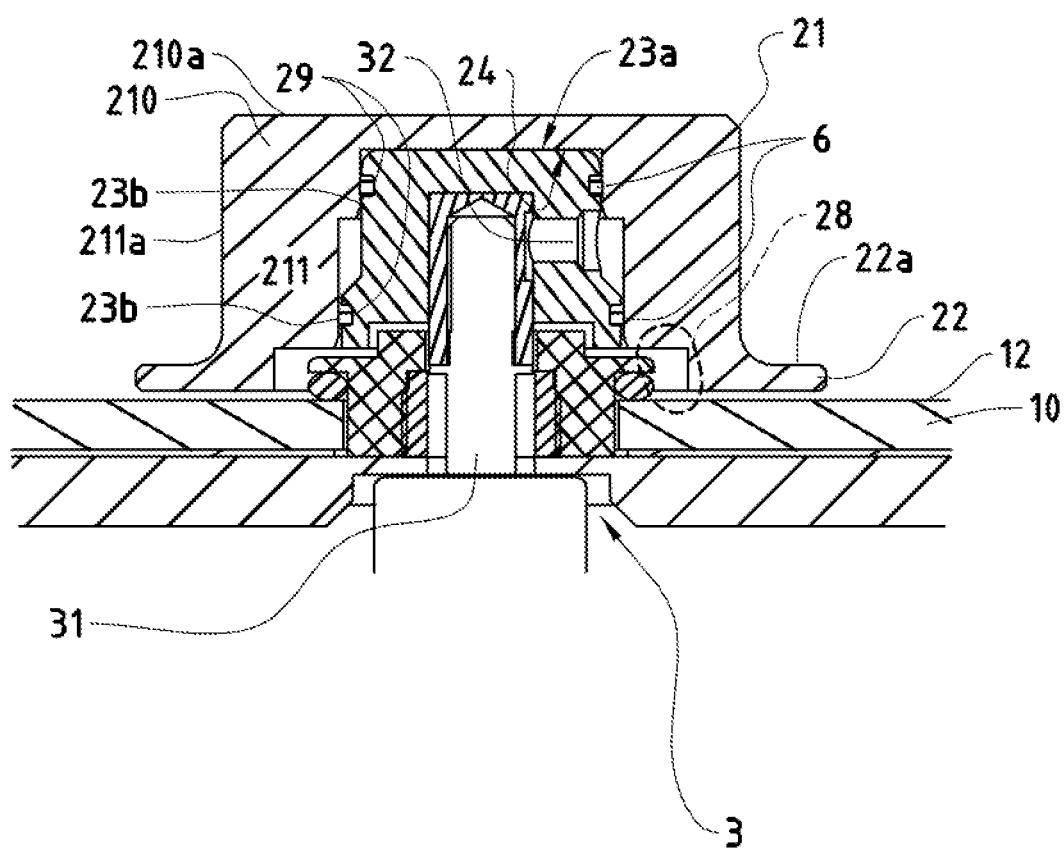
FIG. 6 illustrates a sectional view of an alternative embodiment of the invention using a mode of coupling by friction between the removable sterilizable button and the control support of the box.

According to another variant illustrated by the sectional view of FIG. 6, the mode of coupling between the removable sterilizable button 21 and the control support 20 can be achieved through friction, for example with the aid of one or more O-ring type coupling joints 6 inserted in coupling recesses 29. In FIG. 6, a first coupling recess 29 is disposed just below the cover 210, being in a sufficiently high portion of the control support 20, and a second coupling recess 29 is disposed at the bottom of the control support, in such a way that the forces of friction are distributed on two O-ring joints 6, the compression of which against respective portions of the second inner contact surface 23b of the removable sterilizable button 21 makes it possible at the same time to prevent any pulling out of the latter and to transmit the torque exerted thereon to the encoder 3. However, unlike the magnetic coupling mode, for which the service life is excellent, this solution requires a frequent replacement of joints to ensure the quality of the coupling. All the reference symbols of FIG. 6 which are common to that of FIG. 3 will not be explained again in detail; it can simply be noted that, seen from the outside, there is no perceptible difference with respect to the magnetic coupling mode; only the shapes of the inner contact surfaces of the removable sterilizable button 21 and the shape of the control support 20 possibly differ, but the outer form of the button remains the same and the elements used for coupling remain hidden.

Figure 7:
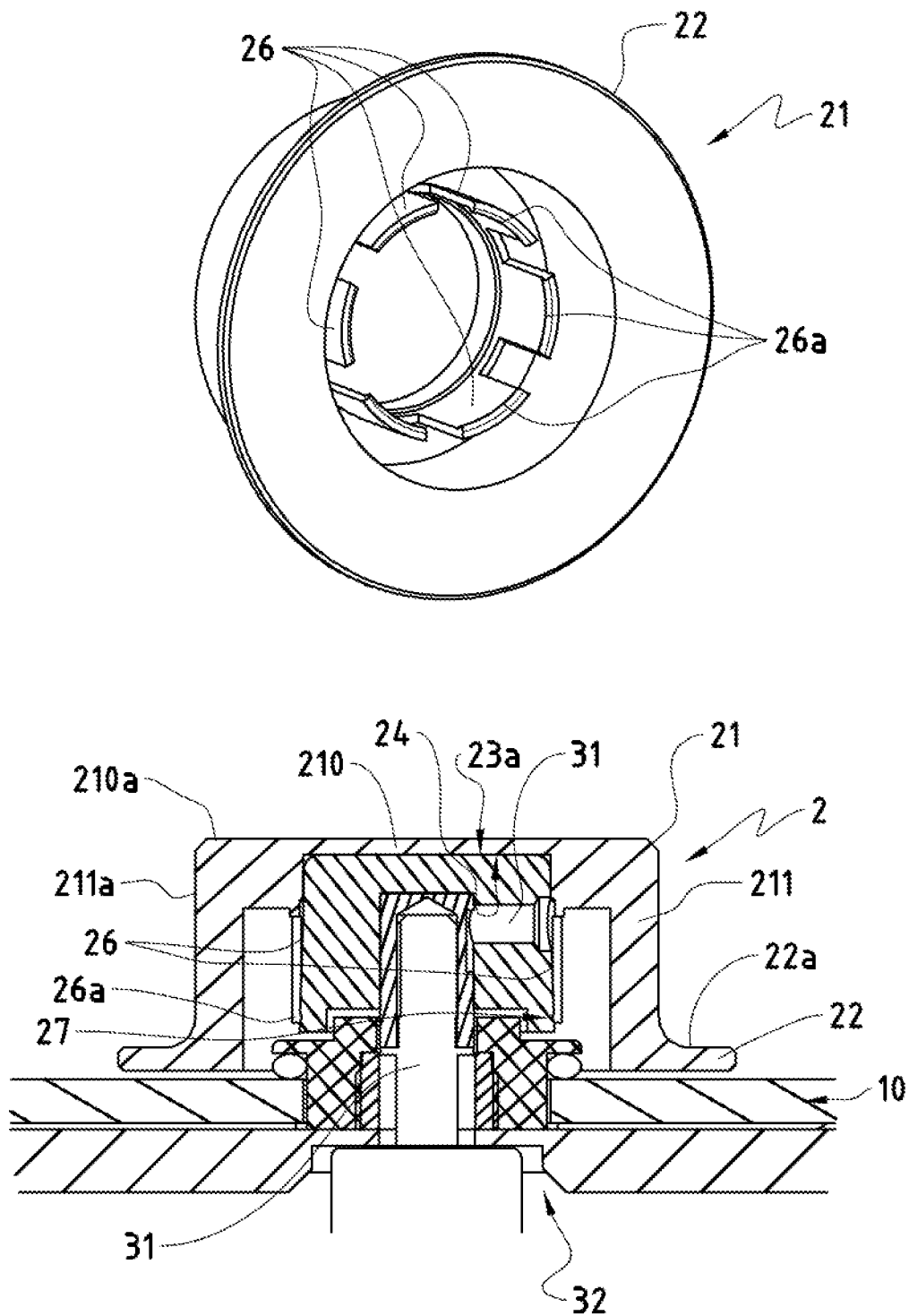
FIG. 7 illustrates a sectional view of an alternative embodiment of the invention using a mode of coupling according to which the removable sterilizable button is snapped on the control support of the box, with a view in perspective from below of the associated sterilizable button highlighting the snap-on fasteners serving in parallel for the driving in rotation of the knob.

According to still another variant illustrated by FIG. 7, the coupling can be achieved through snap-on connection with the aid of at least one elastically deformable snap-on fastener or tongue 26 (in FIG. 7, six of them can be discerned) and composed, for example, of a plastic material, having a lug 26a at its end, which is intended to be inserted in a hooking groove 27 disposed in the control support 20. The co-operation of the lug 26a in the hooking groove 27 makes it possible, on the one hand, to ensure the axial retention of the removable sterilizable button 21 on the control support 20 to prevent any pulling out and also to ensure the transmission of torque. For this purpose, it may be noted that the presence of a cylindrical skirt serving as a snap-on piece, and which would be inserted in an annular groove extending over the entire circumference of the control support 20, would certainly make it possible to act as a means of axial retention, but would not make it possible to fulfil this second function of transmitting torque, which, to the contrary, is all the better carried out the higher the number of snap-on fasteners or tongues and the deeper the corresponding hooking grooves. The proposed arrangement, illustrated in particular in FIG. 7, has the advantage of using at the same time the same elements for the axial retention and for the transmission of the driving in rotation; it has however the drawback of being subject to creep of the plastic element used for the snap-on fasteners or tongues 6, and would therefore require the frequent replacement of the latter to ensure the quality of coupling. Here again, all the reference symbols of FIG. 6 which are common to those of FIG. 3 will not be explained again in detail and there is no perceptible difference seen from the outside with respect to other modes of coupling, as the outer shape of the button remains the same and the elements involved in the coupling are hidden under the cover 210 and the axial skirt 211 of the removable sterilizable button 21.

In the foregoing, the preferred embodiments and the variants have been given solely by way of example, without the intention of limiting the protection sought for the present invention. One skilled in the art will understand that the control system 10 proposed could have any other suitable constitution, possibly slightly different from that described in the foregoing, without departing from the spirit of the present invention nor decreasing the scope conferred for the present invention.

In particular, it is possible to achieve the magnetic coupling in other ways by reversing, for example, the arrangement of the active and passive magnetic parts in the control support and the removable sterilizable button, or even by arranging a number of different permanent magnets distributed between each of the two pieces to assemble. It is likewise possible to use different geometric shapes for the control support 20, as well as for the removable sterilizable button 21, in particular as concerns the axial bearing surfaces and lateral coupling surfaces. Similarly, the number of elements provided for the hooking and the driving in rotation (i.e. the tabs or snap-on fasteners or tongues 26, the lateral coupling recesses 29 for the placement of O-rings 6, etc.) can vary as well as their disposition on the control support 20 and respectively the removable sterilizable button 21, according to needs, insofar as the force necessary for the pulling out remains within the value range similar to that corresponding to the magnetic coupling mode. It is likewise conceivable to combine features relating to different preferred embodiments and different variants previously described without departing from the scope of the present invention.

The invention claimed is:

1. A control system for a micro-motor for dental or surgical use, comprising a control box provided with an adjustment knob rotatable about a rotational axis, wherein said adjustment knob comprises:
   a control support integral with an encoder integrated in said control box and
   a sterilizable button that surrounds and is removably coupled to said control support.

2. The control system for a micro-motor for dental or surgical use according to claim 1, wherein the removable coupling is achieved through friction, through a snap-on connection or magnetically.

3. The control system for a micro-motor for dental or surgical use according to claim 1, wherein said adjustment knob is adapted to select in rotation, and to actuate by pressing, functions which are displayable on a control screen of control the box.

4. The control system for a micro-motor for dental or surgical use according to claim 1, wherein said removable sterilizable button is terminated by a collar extending radially outward.

5. The control system for a micro-motor for dental or surgical use according to claim 1, wherein said removable sterilizable button is coupled to said control support in such a way that, while assembled, an operational play of at least 0.2 mm exists axially between a lower end of said sterilizable button and an outer surface of the control box.

6. The control system for a micro-motor for dental or surgical use according to claim 1, wherein said removable sterilizable button has a central cavity provided with at least one first inner contact surface for coupling to a bearing surface, and wherein means of axial retention and of driving in rotation are arranged on either side of the removable sterilizable button and of the control support.

7. The control system for a micro-motor for dental or surgical use according to claim 6, wherein the central cavity of said removable sterilizable button comes out into an inner peripheral shoulder.

8. The control system for a micro-motor for dental or surgical use according to claim 1, wherein said removable sterilizable button is coupled magnetically to said control support, one active magnetic piece being integrated in said control support and one passive magnetic piece being integrated in said removable sterilizable button, an intensity of exerted magnetic force between said magnetic pieces being within 5 to 15 Newtons.

9. The control system for a micro-motor for dental or surgical use according to claim 8, wherein the central cavity of the removable sterilizable button comprises a second conical inner contact surface, brought to rest when assembled as part of the adjustment knob, against a lateral coupling surface of said control support, the said inner contact surface and lateral coupling surface having an inclination of 15 degrees with respect to the axis of rotation of the said adjustment knob.

10. The control system for a micro-motor for dental or surgical use according to claim 8, wherein said active magnetic piece integrated in the said control support is a first permanent magnet arranged in such a way as to have a magnetization oriented perpendicularly with respect to the axis of rotation of said adjustment knob, and wherein a second permanent magnet is integrated in said removable sterilizable button in such a way as to have a magnetization oriented in a direction of magnetization encompassed in a parallel plane, overlying that of the first permanent magnet.

11. The control system for a micro-motor for dental or surgical use according to claim 8, wherein said active magnetic piece integrated in said control support is a first permanent magnet arranged in such a way as to have a magnetization oriented along the axis of rotation of the said adjustment knob, and wherein a second permanent magnet is integrated in said removable sterilizable button in such a way as to have a magnetization likewise oriented along the axis of rotation of said adjustment knob, but in an opposite direction with respect to that of the said first permanent magnet.

12. The control system for a micro-motor for dental or surgical use according to claim 1, wherein said removable sterilizable button is coupled by friction to the control support by means of O-ring type seals inserted in lateral coupling recesses.

13. The control system for a micro-motor for dental or surgical use according to claim 1, wherein said removable sterilizable button is coupled to the control support with the aid of elastically deformable snap-on fasteners or tongues provided with lugs inserted in hooking grooves.

* * * * *